(12) United States Patent
Fritzinger

(10) Patent No.: US 9,039,745 B2
(45) Date of Patent: May 26, 2015

(54) ONE-PIECE VARIABLE ANGLE LOCKING WASHER

(75) Inventor: Daniel Duane Fritzinger, Warsaw, IN (US)

(73) Assignee: BIOMET MANUFACTURING, LLC, Warsaw, IN (US)

( * ) Notice: Subject to any disclaimer, the term of this patent is extended or adjusted under 35 U.S.C. 154(b) by 78 days.

(21) Appl. No.: 13/456,554

(22) Filed: Apr. 26, 2012

(65) Prior Publication Data

US 2013/0289628 A1    Oct. 31, 2013

(51) Int. Cl.
*A61B 17/80*       (2006.01)
*A61B 17/86*       (2006.01)

(52) U.S. Cl.
CPC ......... *A61B 17/8047* (2013.01); *A61B 17/8057* (2013.01); *A61B 17/8695* (2013.01)

(58) Field of Classification Search
CPC ............... A61B 17/8047; A61B 17/80; A61B 17/8033; A61B 17/8038; A61B 17/8042; A61B 17/86; A61B 17/8665; A61B 17/8695; A61B 2017/867; A61B 2017/8675; A61B 2017/868
USPC .......................................... 411/147, 291, 544
See application file for complete search history.

(56) References Cited

U.S. PATENT DOCUMENTS

| | | | | |
|---|---|---|---|---|
| 3,265,109 | A * | 8/1966 | Hanfland | 411/291 |
| 5,954,722 | A * | 9/1999 | Bono | 606/281 |
| 5,976,141 | A * | 11/1999 | Haag et al. | 606/292 |
| 6,048,344 | A | 4/2000 | Schenk | |
| 7,195,633 | B2 * | 3/2007 | Medoff et al. | 606/309 |
| 7,276,070 | B2 * | 10/2007 | Muckter | 606/71 |
| 7,311,712 | B2 * | 12/2007 | Dalton | 606/71 |
| 7,637,928 | B2 * | 12/2009 | Fernandez | 606/289 |
| 7,766,947 | B2 * | 8/2010 | Hawkes et al. | 606/280 |
| 7,794,482 | B2 * | 9/2010 | Mathieu et al. | 606/290 |
| 7,846,163 | B2 * | 12/2010 | Fourcault et al. | 606/68 |
| 7,862,597 | B2 * | 1/2011 | Gause et al. | 606/290 |
| 7,955,036 | B2 | 6/2011 | Palm | |
| 8,007,523 | B2 * | 8/2011 | Wagner et al. | 606/290 |
| 8,114,140 | B2 * | 2/2012 | Derouet | 606/305 |
| 8,216,283 | B2 * | 7/2012 | Mathieu et al. | 606/280 |
| 2002/0058939 | A1 * | 5/2002 | Wagner et al. | 606/61 |
| 2004/0204762 | A1 | 10/2004 | Ralph et al. | |
| 2004/0254579 | A1 * | 12/2004 | Buhren et al. | 606/71 |
| 2005/0234554 | A1 | 10/2005 | Ralph et al. | |
| 2006/0241618 | A1 | 10/2006 | Gasser et al. | |
| 2008/0249573 | A1 | 10/2008 | Buhren et al. | |
| 2010/0057138 | A1 * | 3/2010 | Murner et al. | 606/308 |
| 2011/0015682 | A1 * | 1/2011 | Lewis et al. | 606/305 |
| 2012/0177462 | A1 | 7/2012 | Fritzinger et al. | |

FOREIGN PATENT DOCUMENTS

FR        2935255 A1    3/2010
WO    WO 2011/085272 A1    7/2011

OTHER PUBLICATIONS

International Search Report and Written Opinion for PCT/US2013/035719, Mailed Jun. 12, 2013, 10 pages.

* cited by examiner

*Primary Examiner* — Christian Sevilla
*Assistant Examiner* — Eric S Gibson
(74) *Attorney, Agent, or Firm* — Taft Stettinius & Hollister LLP; Ryan O. White

(57) ABSTRACT

A variable angle locking washer comprising a body having an outer surface circumferentially disposed between a top surface and a bottom surface, a central bore extending between the top and bottom surfaces, the central bore having a threaded portion and an unthreaded portion, and a plurality of radial slots peripherally positioned along the body, each slot defining a channel that extends between the outer surface of the body and the central bore.

17 Claims, 4 Drawing Sheets

ONE-PIECE VARIABLE ANGLE LOCKING WASHER

TECHNICAL FIELD

The present invention generally relates to locking washers, and more particularly to one-piece washers for variable angle locking systems.

BACKGROUND OF THE INVENTION

The statements in this section merely provide background information related to the present disclosure and should not be construed as constituting prior art.

The use of orthopedic fastening devices, such as bone screws, has greatly aided the medical field in the treatment of bone fractures. More particularly, when treating bone fractures, it is often generally necessary to surgically reposition fragmented bone members in various anatomically acceptable orientations. To fasten the repositioned bone members together in order to facilitate the healing process, bone screws are often used as part of the stabilization process (e.g., either by fastening two or more bone members together, or by securing an orthopedic appliance or bone plate to the bone's surface). Sometimes it is beneficial to orient the bone screw at an angle that is non-collinear to the orthopedic appliance's threaded hole during the stabilization process—for instance, to avoid poor bone stock or fracture lines.

One variable angle locking washer assembly includes two spherical shaped stacked washers having a spring functioning member positioned therebetween. When a screw is used to install the assembly to a humeral plate, the spring member presses the two outer washers against the walls of the plate material, thereby providing friction to securely hold the washers in place as the bone screws are tightened. One drawback to this three-piece design, however, is that there are three separate components which must be assembled in a specific orientation to the humeral plate. As these components are fairly small, the assembly operator must pay close attention when performing the assembly. There is a need for a variable angle locking assembly that is not only easy to manufacture, but is also easy to use and manipulate as part of a stabilization process.

The present invention is intended to improve upon and resolve some of these known deficiencies within the relevant art.

SUMMARY OF THE INVENTION

In accordance with one aspect of the present invention, a variable angle locking washer is provided comprising a body having an outer surface circumferentially disposed between a top surface and a bottom surface, a central bore extending between the top and bottom surfaces, the central bore having a threaded portion and an unthreaded portion, and a plurality of radial slots peripherally positioned along the body, each slot defining a channel that extends between the outer surface of the body and the central bore.

In accordance with yet another aspect of the present invention, a variable angle locking washer assembly is provided comprising a locking washer having a plurality of radial slots peripherally positioned along an outer surface of the washer, each slot defining a channel that extends between the outer surface and a central bore having a threaded portion and an unthreaded portion; a plate material having an opening defining a mating pocket configured to receive the locking washer; and a screw including a head portion having helical threads and an elongated shaft portion extending from the head portion, the shaft portion being insertable into the central bore at more than one angle relative to a first axis to lock the screw to the plate material. In accordance with certain aspects of the present invention, the first axis is arranged in substantially perpendicular correspondence to a horizontal plane traversing the washer at a position substantially halfway between a top surface and a bottom surface.

In still another aspect of the present invention, the variable angle locking washer assembly comprises a screw including a head portion having helical threads and an elongated shaft portion extending from the head portion; a plate material having an opening; and a locking washer having a central bore and plurality of radial slots peripherally positioned along an outer surface of the washer. In accordance with this embodiment, the central bore has a threaded portion and an unthreaded portion, wherein the threaded portion is configured to mate with the helical threads on the head portion of the screw to lock the screw to the plate material at more than one angle relative to a first axis. In accordance with certain aspects of the present invention, the first axis is arranged in substantially perpendicular correspondence to a horizontal plane traversing the washer at a position substantially halfway between a top surface and a bottom surface.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although it is contemplated that any method and materials similar or equivalent to those described herein can be used in the practice or testing of the present invention, various illustrative methods and materials are now described. Unless otherwise noted, it should be understood and appreciated that the techniques employed or contemplated herein can be standard methodologies well known to one of ordinary skill in the art and that the various materials, methods and examples disclosed herein are illustrative only and not intended to be limiting.

Figure 1:
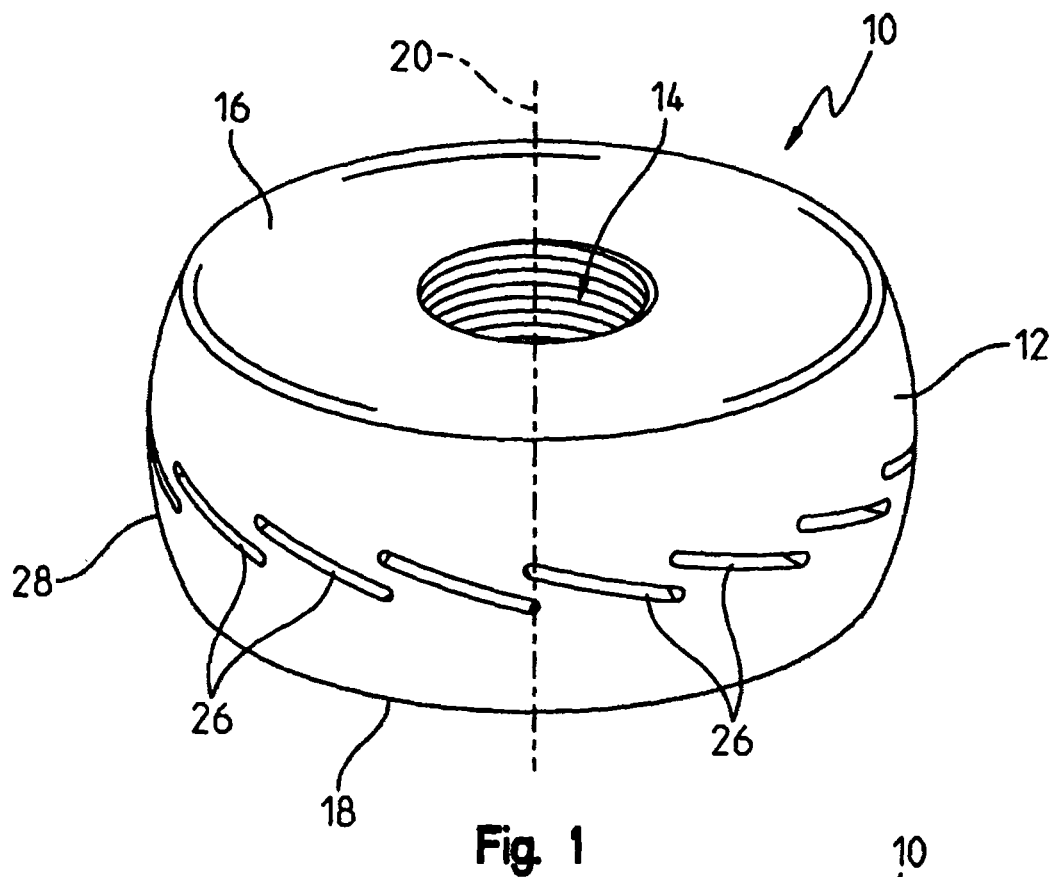
FIG. 1 is an elevated perspective view of an illustrative variable angle locking washer in accordance with the teachings of the present invention.
Figure 2:
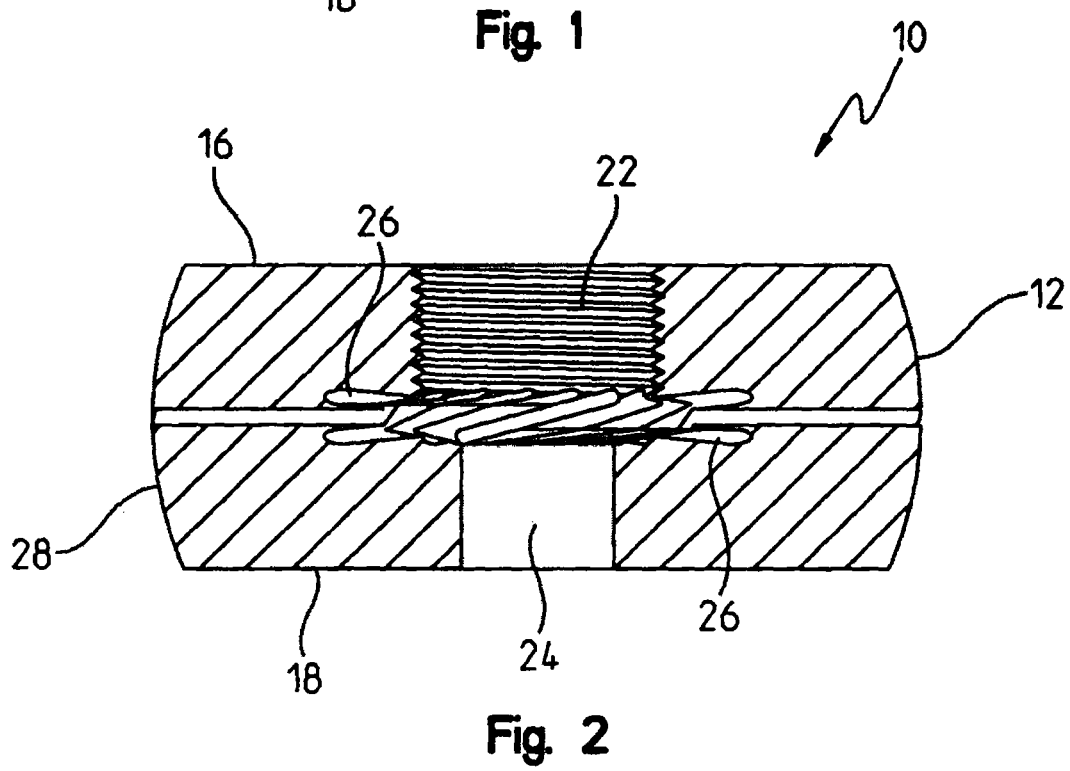
FIG. 2 is a cross-sectional side view of the illustrative variable angle locking washer of FIG. 1.

FIG. 1 is an elevated perspective view of an illustrative variable angle locking washer in accordance with the teachings of the present invention. In accordance with certain aspects of the present invention, the washer 10 comprises a hollow cylindrical body 12 having an outer diameter that is substantially spherical in shape. The hollow cylindrical body 12 is defined by a bore 14 that extends from a top surface 16 to a bottom surface 18 along a central axis 20. As best shown in FIG. 2, the bore includes a threaded portion 22 and an unthreaded portion 24. In accordance with certain embodiments, the threaded portion 22 extends from the top surface 16 of the cylindrical body 12 about halfway through the bore 14, while the unthreaded portion 24 extends from about midway through the bore 14 to the bottom surface 18 of the cylindrical body 12.

Figure 3:
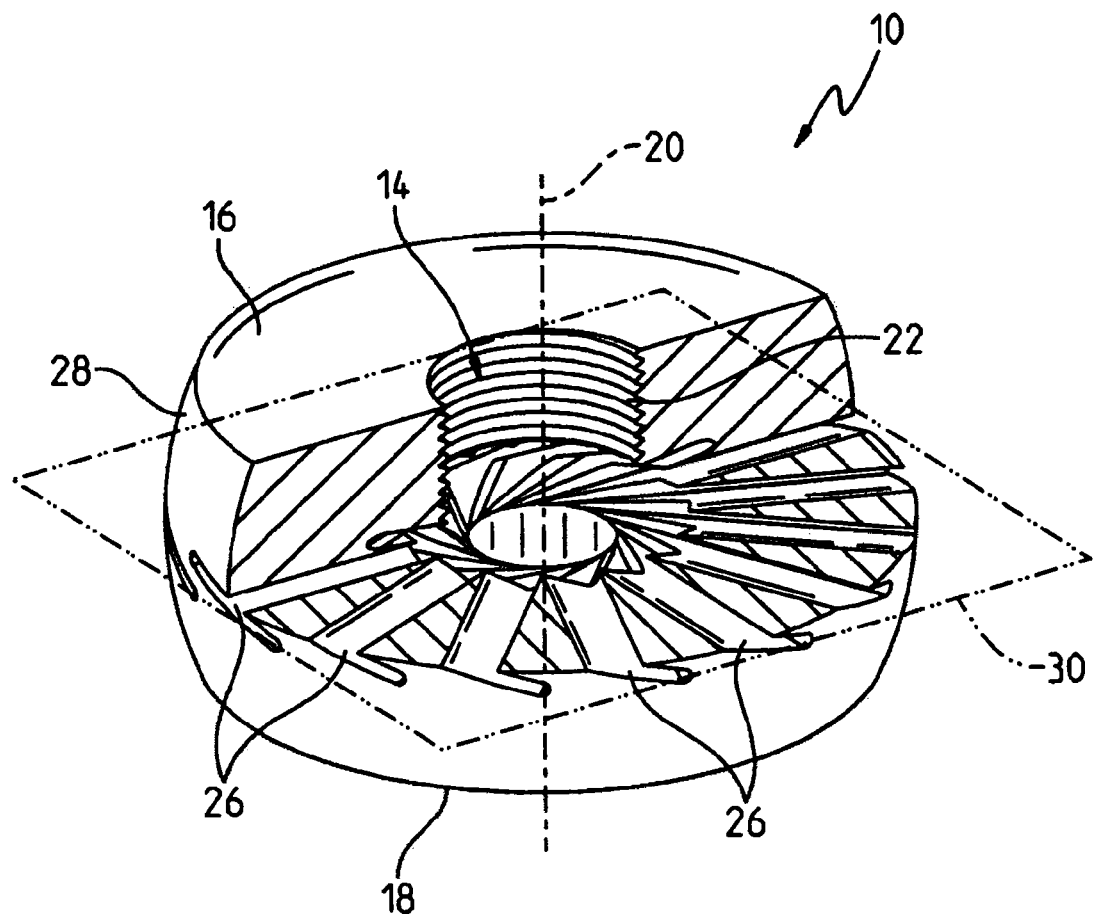
FIG. 3 is an elevated partial cross-sectional perspective view of the illustrative variable angle locking washer of FIG. 1.

The washer 10 further comprises a series of slots or channels 26 that radially extend centrally inward towards the bore 14 from the outer surface of a sidewall 28 defined between the top surface 16 and the bottom surface 18 of the cylindrical body 12. In accordance with certain aspects of the present invention, the slots 26 are located along the entire circumferential periphery of the sidewall 28 and are positioned substantially about a horizontal plane 30 that passes through (traverses) the cylindrical body 12 between the top and bottom surfaces 16, 18 (see FIG. 3). According to certain aspects of the present invention, the horizontal plane 30 is disposed between and substantially parallel to the top and bottom surfaces 16, 18. In certain specific embodiments, the horizontal plane 30 is positioned substantially halfway between the top and bottom surfaces 16, 18 of the body 12. In accordance with this embodiment, at least a portion of each slot 26 passes through and intersects the horizontal plane 30 as the slot extends between the outer diameter of the sidewall 28 and the central bore 14. Further, as can specifically be seen in FIGS. 2 and 3, in accordance with certain embodiments, the series of slots 26 centrally converge in a location along the bore 14 where the threaded portion 22 and the unthreaded portion 24 adjoin.

In accordance with certain aspects of the present invention, the radial slots 26 extend all the way from the sidewall 28 to the bore 14 (i.e., they are not blind slots that terminate prior to reaching the central bore). While the specific dimensions of the radial slots can be adjusted as desired, in accordance with certain illustrative embodiments, each slot 26 has a uniform (e.g., straight) shape as it traverses the body 12 of the washer 10 from the sidewall 28 to the bore 14.

Figure 4:
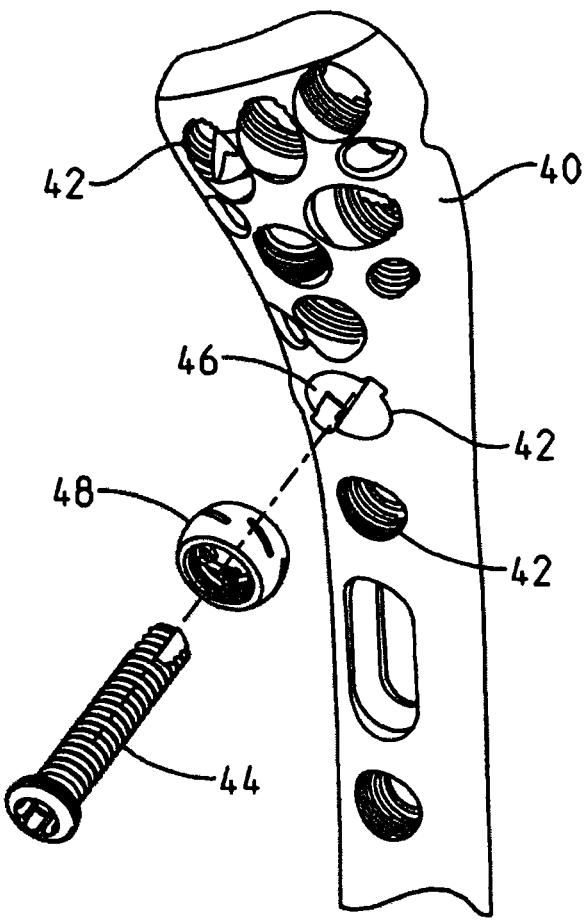
FIG. 4 is an exploded, partial perspective view of an illustrative variable angle locking washer prior to being assembled into a bone plate in accordance with the teachings of the present invention.
Figure 5:
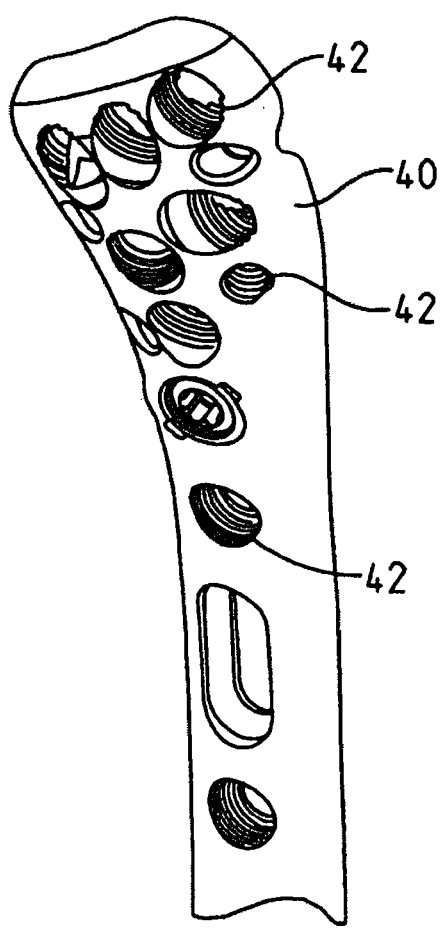
FIG. 5 is a partial perspective view of the illustrative variable angle locking washer assembly of FIG. 4 after being assembled into the bone plate.

FIG. 4 is an exploded, partial perspective view of an illustrative variable angle locking washer assembly in accordance with the teachings of the present invention. In accordance with this illustrative embodiment, a plate material 40 (e.g., bone plate) having one or more through holes 42 is configured to receive a screw 44 that concurrently mounts the plate material to bodily tissue such as, without limitation, bone (not shown). Because there are instances where the screw 44 is intended to be angled other than non-collinearly to the axis of the threaded hole 42 (see reference numeral 62 of FIG. 7), it is advantageous to provide a mechanism that allows the screw to be oriented at angles and rotational positions off-axis to the plates' threaded hole axis 62, while being secured to the plate material. At the same time, the angle of the screw 44 with respect to the plate material 40 may not necessarily be predetermined, so providing flexibility as to the angular orientation of the screw may be advantageous in accordance with certain aspects of the present invention. To accomplish this angular variability, a number of walls can be machined into the through hole 42 of the plate material 40 to create mating pocket 46 for holding a washer 48 in place with respect to the plate material 40 when the screw 44 is tightened thereto (see FIG. 5). While those of skill in the art will understand and appreciate that the size of the through hole 42 is directly related to the range of angularity to which the screw 44 can be installed into the plate material 40 (e.g., as the screw is rotated off-axis, eventually the shank or body of the screw will contact the edge of the plate hole), it is particularly useful if the mating pocket 46 is shaped in such a manner that the washer 48 is prevented from spinning when the screw is tightened to the plate. One exemplary way to prevent the washer 48 from spinning is to size the washer such that it is slightly thicker than the mating pocket 46 when in its free state. Another such exemplary option for preventing the washer from spinning is to create a light interference press-fit between the washer 48 and the through hole 42. Those of skill within the art will understand and appreciate that there are several ways to achieve such an interference press-fit relationship, however, in accordance with certain aspects of the present invention, the outer surfaces of the washer and/or through hole could be roughened, serrated or knurled.

Figure 6:
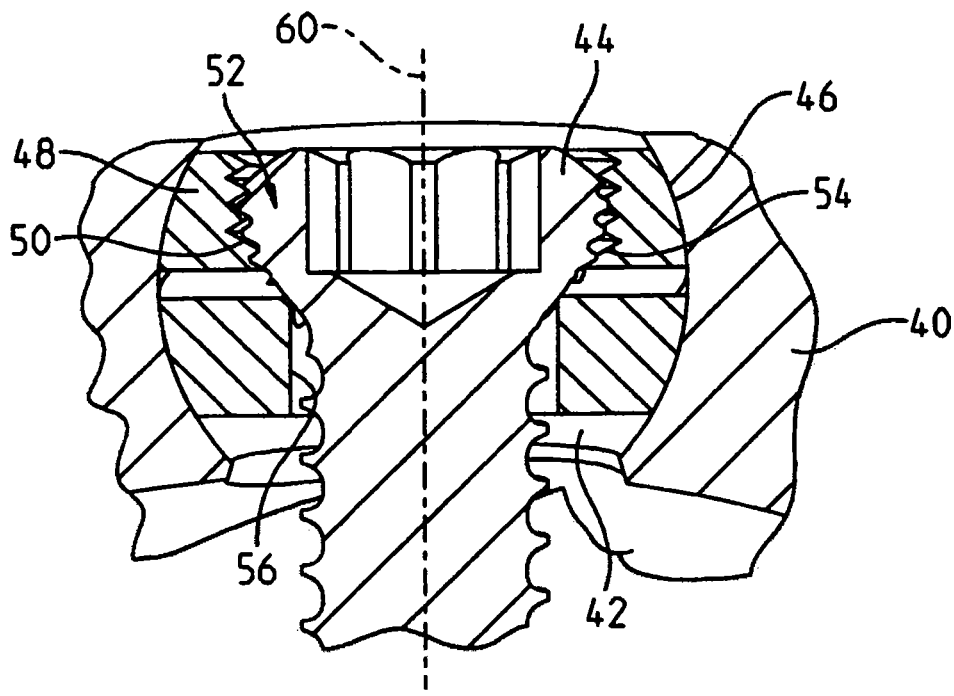
FIG. 6 is a cross-sectional side view of an illustrative variable angle locking washer having an on-axis assembly to a bone plate in accordance with the teachings of the present invention.
Figure 7:
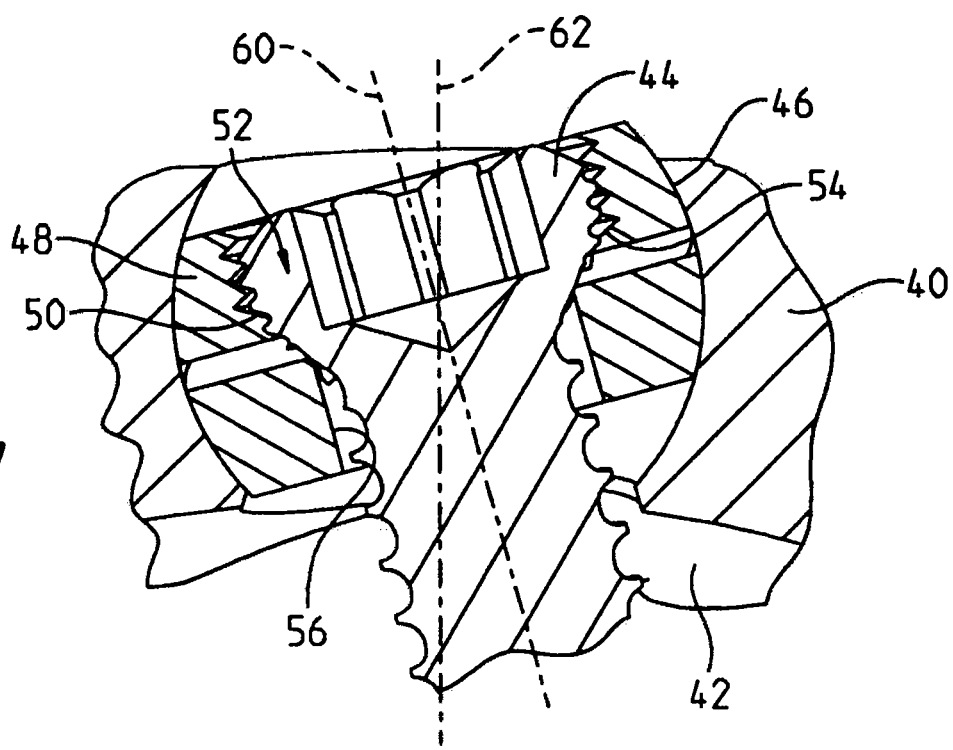
FIG. 7 is a cross-sectional side view of an illustrative variable angle locking washer having an off-axis assembly to a bone plate in accordance with the teachings of the present invention.

As shown in FIGS. 6 and 7, in accordance with certain aspects of the present invention, the screw 44 used to mount the plate material 40 to bodily tissue is a locking screw having helical threads 50 extending around the circumference of its head 52. Depending on the use and application of the locking screw 44, it should be understood and appreciated that the helical threads 50 may be spherical, conical or spherical-conical in thread form. To install the plate material 40 to bodily tissue, the washer 48 is pre-loaded in the mating pocket 46 of the plate material 40 and the screw head 52 is then threaded to the washer 48. As the screw 44 is tightened, the threads 50 of the screw head 52 mate with and then press against the shoulder of the washer at the unthreaded portion 56 to spread the washer 48 apart linearly. More particularly, as those of skill in the art will understand and appreciate herein, the radial slots 26 of the washer 48 are oriented in such a manner that the washer functions as a spring member—i.e., it has a restoring force when compressed. As the washer 48 is subjected to an external compressive load or pressure, the resultant pressure differential causes the washer to expand/stretch linearly along the axis of the through hole 42. In other words, when the screw head 52 is threaded into the washer 48, it acts like a jackscrew to spread the upper and lower washer halves apart.

Many conventional variable angle locking washer assemblies utilized a three piece design. In accordance with these designs, two washers were stacked together with a spring positioned therebetween. The function of the spring was to press the two washers against the walls of the through hole mating pocket of the plate material, thereby providing friction to hold the washers in place during tightening of the bone screws. The present invention renders the three piece washer design unnecessary by allowing the spring-like feature to still be achieved with a single washer assembly piece (i.e., the array of slots 26 machined into the cylindrical body of the washer function as the spring in the three piece design). In accordance with certain aspects of the present invention, the washer (in its free state) can be slightly dimensionally larger than the mating pocket 46 of the plate material 40. According to this embodiment, when the washer 48 is installed in the mating pocket 46 of the plate material 40, the threaded portion 54 of the bore functions equivalently to the threaded washer in the three piece design while the unthreaded portion 56 functions as the conventional through hole washer.

As explained above, in accordance with certain aspects of the present invention, it may be desirable to orient the bone screw 44 at an angle that is off-axis to the plates' threaded hole 42—for instance, to avoid poor bone stock or fracture lines or to capture a particular bone fragment. This angular variability can be appreciated with reference to FIGS. 6 and 7. More particularly, while FIG. 6 depicts an illustrative variable angle locking washer 48 having an on-axis assembly to a plate material 40, FIG. 7 depicts the locking washer 48 being installed off-axis to the threaded hole 42 (i.e., the axis of the screw 44 is represented by reference numeral 60 and the axis of the threaded hole is represented by reference numeral 62).

The aforementioned may, in exemplary forms thereof, be manufactured from titanium or stainless steel. However, it should be understood and appreciated herein that any suitable material may be utilized to fabricate the aforementioned components, including, without limitation, plastics, ceramics, metals, and alloys of the foregoing.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

The invention is claimed is:

1. A variable angle locking washer comprising: a body of unitary, one-piece construction formed from a resiliently deformable material having an outer surface circumferentially disposed between a top surface and a bottom surface, the outer surface defining a sidewall that surrounds an entire periphery of the unitary body, the sidewall having a constant convex curvature that transitions between the top surface and the bottom surface;

a central bore extending between the top and bottom surfaces, the central bore having a threaded portion and an unthreaded portion; and a plurality of radial slots peripherally positioned along the unitary body, each radial slot defining an channel that extends between the outer surface of the unitary body and the central bore;

wherein each radial slot is disposed parallel to a diagonal axis that intersects the top surface of the unitary body, and wherein each radial slot at least partially intersects a line defining a maximum peripheral circumference of the sidewall; and wherein the top surface is capable of expanding axially away from the bottom surface about the central bore while remaining substantially parallel thereto.

2. The variable angle locking washer of claim 1, wherein the plurality of radial slots centrally converge in a location along the central bore where the threaded portion and the unthreaded portion meet.

3. The variable angle locking washer of claim 1, wherein the central bore is configured to lockably receive a screw insertable therethrough at more than one angle relative to a central axis.

4. The variable angle locking washer of claim 3, wherein the screw further includes helical threads that are configured to lockably mate with the threaded portion of the bore.

5. The variable angle locking washer of claim 4, wherein the plurality of radial slots are configured to linearly expand the washer against a surface of a plate material as the helical threads lockably mate with the threaded portion of the bore, the surface of the plate material being associated with a mating pocket that is configured to receive the washer.

6. The variable angle locking washer of claim 5, wherein the plate material is a bone plate.

7. The variable angle locking washer of claim 3, wherein the central axis is arranged in substantially perpendicular correspondence to a horizontal plane traversing the unitary body at a position substantially halfway between the top surface and the bottom surface.

8. A variable angle locking washer assembly comprising: a locking washer of unitary, one-piece construction formed from a resiliently deformable material having a plurality of radial slots peripherally positioned along an outer surface of the unitary locking washer, each radial slot defining a channel that extends between the outer surface and a central bore having a threaded portion and an unthreaded portion, wherein the outer surface is circumferentially disposed between a top surface and a bottom surface and defines a sidewall that surrounds an entire periphery of the unitary locking washer, the sidewall having a constant convex curvature that transitions between the top surface and the bottom surface;
 a plate material having an opening defining a mating pocket configured to receive the unitary locking washer; and
 a screw including a head portion having helical threads and an elongated shaft portion extending from the head portion, the shaft portion being insertable into the central bore at more than one angle relative to a central axis to lock the screw to the plate material;
 wherein each radial slot is disposed parallel to a diagonal axis that intersects the top surface of the unitary locking washer, and wherein each radial slot at least partially intersects a line defining a maximum peripheral circumference of the sidewall; and
 wherein the top surface is capable of expanding axially away from the bottom surface about the central bore while remaining substantially parallel thereto.

9. The variable angle locking washer assembly of claim 8, wherein the plurality of radial slots centrally converge in a location along the central bore where the threaded portion and the unthreaded portion meet.

10. The variable angle locking washer assembly of claim 8, wherein the helical threads on the head portion of the screw are configured to mate with the threaded portion of the central bore as the screw is locked to the plate material.

11. The variable angle locking washer assembly of claim 8, wherein the central axis is arranged in substantially perpendicular correspondence to a horizontal plane traversing the unitary locking washer at a position substantially halfway between the top and bottom surfaces.

12. The variable angle locking washer assembly of claim 8, wherein the plurality of radial slots are configured to linearly expand the unitary locking washer against the mating pocket as the screw is locked to the plate material.

13. A variable angle locking washer assembly comprising:
 a screw including a head portion having helical threads and an elongated shaft portion extending from the head portion;
 a plate material having an opening; and
 a locking washer of unitary, one-piece construction formed from a resiliently deformable material having a central bore and plurality of radial slots peripherally positioned along an outer surface of the unitary locking washer, the outer surface being circumferentially disposed between a top surface and a bottom surface and defining a sidewall that surrounds an entire periphery of the unitary locking washer, the sidewall having a constant convex curvature that transitions between the top surface and the bottom surface;
 wherein the central bore has a threaded portion and an unthreaded portion;
 wherein each radial slot is disposed parallel to a diagonal axis that intersects the top surface of the unitary locking washer, and wherein each radial slot at least partially intersects a line defining a maximum peripheral circumference of the sidewall;
 wherein the threaded portion is configured to mate with the helical threads on the head portion of the screw to lock the screw to the plate material at more than one angle relative to a central axis; and
 wherein the top surface is capable of expanding axially away from the bottom surface about the central bore while remaining substantially parallel thereto.

14. The variable angle locking washer assembly of claim 13, wherein each of the plurality of radial slots define a channel extending between the outer surface and the central bore.

15. The variable angle locking washer assembly of claim 13, wherein the plurality of radial slots centrally converge in a location along the central bore where the threaded portion and the unthreaded portion meet.

16. The variable angle locking washer assembly of claim 13, wherein the central axis is arranged in substantially perpendicular correspondence to a horizontal plane traversing the unitary locking washer at a position substantially halfway between the top and bottom surfaces.

17. The variable angle locking washer assembly of claim 13, wherein the plurality of radial slots are configured to linearly expand the unitary locking washer against a surface of a plate material as the helical threads lockably mate with the threaded portion of the bore, the surface of the plate material being associated with a mating pocket that is configured to receive the unitary locking washer.

* * * * *

UNITED STATES PATENT AND TRADEMARK OFFICE
CERTIFICATE OF CORRECTION

PATENT NO. : 9,039,745 B2  
APPLICATION NO. : 13/456554  
DATED : May 26, 2015  
INVENTOR(S) : Daniel Duane Fritzinger It is certified that error appears in the above-identified patent and that said Letters Patent is hereby corrected as shown below:

In the Claims

Column 6, Claim 1, line 46, please change the word "an" to "a"

Signed and Sealed this
Twenty-seventh Day of October, 2015

Michelle K. Lee
*Director of the United States Patent and Trademark Office*